(12) United States Patent
Seale et al.

(10) Patent No.: US 8,067,542 B1
(45) Date of Patent: Nov. 29, 2011

(54) AMINO ACID SEQUENCE VARIANT ALFALFA ANTIFUNGAL PROTEIN AND ITS USE IN PLANT DISEASE CONTROL

(75) Inventors: Jeffrey W Seale, Ballwin, MO (US); Paul B. Vordtriede, Kansas City, MO (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

(21) Appl. No.: 12/728,443

(22) Filed: Mar. 22, 2010

Related U.S. Application Data

(62) Division of application No. 10/707,039, filed on Nov. 17, 2003, now Pat. No. 7,728,190.

(51) Int. Cl.
*A61K 36/00* (2006.01)
*C07K 1/02* (2006.01)
*C07K 16/00* (2006.01)

(52) U.S. Cl. ........................ 530/370; 530/379
(58) Field of Classification Search .............. None
See application file for complete search history.

(56) References Cited

U.S. PATENT DOCUMENTS

| | | | | |
|---|---|---|---|---|
| 6,121,436 | A | * | 9/2000 | Liang et al. .................. 536/23.6 |
| 6,316,407 | B1 | | 11/2001 | Liang et al. |
| 6,329,504 | B1 | | 12/2001 | Liang et al. |

OTHER PUBLICATIONS

DeSamblanx et al. 1997, The Journal of Biological Chemistry 272:1171-1179.*
Papadopoulou E, et al., *Critical Area Computation via Voronoi Diagrams*, IEEE Transactions on Computer-Aided Design of Integrated Circuits and Systems 18(4):463-474 (1999).
Papadopoulou E, et al., *The Loo Voronoi Diagram of Segments and VLSI Applications*, Int. J. Comput. Geom. Appl. 11(5):503-528 (2001).
DeSamblanx et al., *Mutational Analysis of a Plant Defensin from Radish (Raphanus sativus L.) Reveals Two Adjacent Sites Important for Antifungal Activity*, J. Biol. Chem. 272: 1171-1179 (1997).

* cited by examiner

*Primary Examiner* — Li Zheng
(74) *Attorney, Agent, or Firm* — Timothy K. Ball, Esq.

(57) ABSTRACT

The present invention relates to an antifungal protein, AlfAFP1, which is a modified form of an antifungal protein isolated from *Medicago* plants, the modified form exhibiting enhanced anti-fungal activity for controlling fungal pathogenesis in plants. A method for inhibiting fungal colonization of plants is described which includes preparation of nucleotide sequences encoding the modified antifungal protein, preparation of vectors containing the nucleotide coding sequence, and methods for transforming plants with the nucleotide sequences. The polypeptide can be formulated into compositions useful in controlling plant pathogenic fungi.

3 Claims, 1 Drawing Sheet

```
AlfaAFP    RTCENLADKYRGPCF--SGCDTHCTTKENAVSGRC-RDD-FR-CWCTKRC
y-thi      KICRRRSAGFKGPCMSNKNCAQVCQQ-EGWGGGNCDGP--FRRCKCIRQC
RsAFP      QKLCERPSGTWSGVCGNNNACKNQCINLEKARHGSCNYVFPAHKCICYFPC
```

AMINO ACID SEQUENCE VARIANT ALFALFA ANTIFUNGAL PROTEIN AND ITS USE IN PLANT DISEASE CONTROL

CROSS-REFERENCE TO RELATED APPLICATIONS

This application is a divisional of U.S. application Ser. No. 10/707,039, filed Nov. 17, 2003, which issued as U.S. Pat. No. 7,728,190 on Jun. 6, 2010, the disclosure of which is incorporated herein by reference in its entirety.

BACKGROUND OF INVENTION

The present invention relates to new antifungal polypeptides that exhibit broad-spectrum antifungal activity against pathogenic and other fungi. Specifically, the present invention relates to a variant amino acid sequence defensin protein derived from an alfalfa antifungal protein and its use as an antifungal polypeptide in plant disease control against plant pathogenic fungi. The present invention relates to the antifungal polypeptides obtainable from plants in the genus *Medicago*. The antifungal polypeptides may be applied directly to a plant, applied to a plant in the form of microorganisms that produce the polypeptides, or the plants may be genetically modified to produce the polypeptides. The present invention also relates to microorganisms and plants transformed with DNA sequences encoding the amino acid sequence variant alfalfa antifungal protein (AFP), and compositions useful in controlling plant pathogenic fungi.

Protection of agriculturally important crops from insects and diseases has become a major concern in the agricultural industry. Fungus infection is a particular problem in damp climates and is additionally a major concern during crop storage. Plants have developed a certain degree of natural resistance to pathogenic fungi; however, modern growing methods, harvesting and storage systems frequently provide a favorable environment for plant pathogens.

Adding to the problem is the number of different fungi that may cause problems. Fungal damage can be caused by a fungus of genera such as *Alternaria, Ascochyta, Botrytis, Cercospora, Colletotrichum, Diplodia, Erysiphe, Fusarium, Gaeumanomyces, Helminthosporium, Macrophomina, Nectria, Peronospora, Phoma, Phymatotrichum, Phytophthora, Plasmopara, Podosphaera, Puccinia, Pythium, Pyrenophora, Pyricularia, Rhizoctonia, Scerotium, Sclerotinia, Septoria, Thielaviopsis, Uncinula, Venturia*, and *Verticillium* among others. Therefore, fungicidal compounds are not always effective because antifungal activity associated with a particular compound may be limited to a few species.

One approach to inhibiting plant pathogenic activity has been to identify and isolate compounds that exhibit high levels of activity against these pathogens. Several classes of polypeptides and proteins exhibiting antifungal activity against a variety of plant pathogenic fungi have been isolated (Bowles, 1990; Brears et al., 1994). The antifungal polypeptides and proteins include chitinases, cysteine-rich chitin-binding proteins, β-1,3-glucanases, permatins (including zeamatins), thionins, ribosome-inactivating proteins, and non-specific lipid transfer proteins. These proteins are believed to play important roles in plant defense against fungal infection. The use of natural protein products to control plant pathogens has been demonstrated, for example, in EPO 0 392 225.

Recently, another group of plant proteins has been found to function as defensins in combating infections by plant pathogens (PCT International Publication WO 93/05153). The plant defensins are a family of small proteins that possess potent antimicrobial and antifungal activity (for review, see Broekaert et al., 1997). The plant defensins are characterized by a conserved pattern of eight cysteine residues forming what has been referred to as a cysteine-stabilized α-helix that stabilizes folding characteristics of these proteins (Kobayashi et al., 1991). Multiple sequence comparisons of several defensins reveal that these proteins have eight cysteines, two glycines, an aromatic residue, and one acidic residue in common (Broekaert et al., 1995). This small degree of sequence conservation suggests that the cysteine-stabilized α-helix motif provides a scaffold for accommodating a variety of antimicrobial activities. Two small cysteine-rich proteins isolated from radish seed that exhibit this conserved motif, Rs-AFP1 and Rs-AFP2, were found to inhibit the growth of many pathogenic fungi when the pure protein was added to an in vitro antifungal assay medium. Transgenic tobacco plants containing the gene encoding Rs-AFP2 protein were found to be more resistant to attack by fungi than non-transformed plants. Defensin amino acid sequence variants of the radish Rs-AFP2 were identified that exhibited improved antifungal activity (De Samblanx et al, 1997). Certain amino acid modifications to non-conserved amino acids based on the alignment of the protein with a host of other plant defensins resulted in improvement in the antifungal activity of Rs-AFP2, particularly in the presence of $Ca^{2+}$. The amino acid variants all contained an arginine substitution for a naturally occurring amino acid, which increased the net positive charge on the resulting amino acid sequence variant.

Proteins similar to radish seed Rs-AFP2 have been isolated from seeds of other plants (WO 93/105153; Broekaert et al., 1995). All the proteins in this group share similarity in their amino acid sequence, but differ in their antifungal activities against various fungi, especially in the presence of different mono- and divalent salts. The activity of some antifungal proteins is dramatically reduced in the presence of 1 mM $CaCl_2$ and 50 mM KCl (Terras et al., 1992). The usefulness of an antifungal protein for genetically engineering plant disease resistance can be greatly influenced by the sensitivity of the antifungal activity to salt concentration, since metal ions such $K^+$, $Na^+$, $Ca^{2+}$ and $Mg^{2+}$ are required for normal physiological functions and are therefore abundantly present in plant cells. Furthermore, the small size of these proteins suggests that minor modifications to the amino acid sequence could effect dramatic changes in the biological activity of the proteins.

Recombinant DNA technology has recently led to the development of transgenic plants that can express proteins that have antimicrobial activity against certain pests. For example, methods for transforming a wide variety of different dicotyledonous plants and obtaining transgenic plants have been reported in the literature (see Gasser and Fraley, 1989; Fisk and Dandekar, 1993; Christou, 1994). Similarly, methods for producing transgenic plants among the monocotyledonous plants are also well documented. Successful transformation and plant regeneration have been achieved in asparagus (*Asparagus officinalis*; Bytebier et al. 1987), barley (*Hordeum vulgare*; Wan and Lemaux, 1994), maize (*Zea mays*; Rhodes et al. 1988; Gordon-Kamm et al., 1990; Fromm et al. 1990; Koziel et al., 1993), oats (*Avena sativa*; Somers et al., 1992), orchardgrass (*Dactylis glomerata*; Horn et al., 1988), rice (*Oryza sativa*; including indica and japonica varieties; Toriyama et al., 1988; Zhang et al., 1988; Luo and Wu 1988; Zhang and Wu, 1988; Christou et al., 1991), rye (*Secale cereale*; De la Pena et al., 1987), sorghum (*Sorghum bicolor*; Cassas et al., 1993), sugar cane (*Saccharum* spp.; Bower and Birch, 1992), tall fescue (*Festuca arundinacea*; Wang et al., 1992), turfgrass (*Agrostis palustris*; Zhong et al., 1993), and wheat (*Triticum aestivum*; Vasil et al., 1992; Troy Weeks et al., 1993; Becker et al., 1994).

A number of publications have discussed the use of plant and bacterial glucanases, chitinases, and lysozymes produced in transgenic plants exhibiting increased resistance to various microorganisms such as fungi (EP 0 292 435, EP 0 290 123, EP 0 392 225, EP 0 307 841, EP 0 332 104, EP 0 440 304, EP 0 418 695, EP 0 448 511, WO 91/06312, WO 88/00976, WO 90/07001 and U.S. Pat. No. 4,940,840). The protection obtained from expression of osmotin-like proteins is discussed in WO 91/18984. Alfalfa AFP (AlfAFP) is a member of the plant defensin family isolated from the seeds of alfalfa, *Medicago sativa*, and exhibits broad spectrum antifungal activity including activity against the potato pathogen *Verticillium dahliae* and the wheat pathogen *Fusarium graminearum* (U.S. Pat. Nos. 6,121,436, and 6,316,407). Expression of AlfAFP in potato was shown to confer resistance to early dying disease caused by *Verticillium* in potato (Gao et al, 2000). However, plants expressing AlfAFP also show a reduction in potato tuber size. AlfAFP was unable to provide an adequate level of protection to plants infected with *Fusarium* head blight even though the protein exhibited in vitro efficacy against *Fusarium graminearum*.

There is thus a continuing need to identify biocidal compounds, particularly those that will be effective against plant pathogenic fungi, whether applied as compositions directly to an infected plant or expressed in transgenic plants in amounts sufficient to provide protection against the pathogens.

SUMMARY OF THE INVENTION

The present invention provides an antifungal polypeptide comprising an amino acid sequence shown in SEQ ID NO:2, and biologically functional equivalents thereof, that can be produced or synthesized by any suitable method known in the art, including direct chemical synthesis, synthesis in heterologous biological systems such as microbial, plant, and animal systems, tissue cultures, cell cultures, or in vitro translation systems.

The present invention also provides a nucleotide sequence encoding an antifungal polypeptide as set forth in SEQ ID NO:2 and constructs and methods for inserting said nucleotide sequences into host cells for expression of the polypeptide. The nucleotide sequence encoding SEQ ID NO:2 comprises a modified AlfAFP gene designated as an AlfAFP1 coding sequence exhibited by the nucleotide sequence as set forth in SEQ ID NO: 1. The nucleotide sequence may be a cDNA molecule, an RNA molecule, a native nucleotide sequence (i.e., naturally occurring), or a nucleotide sequence artificially assembled for example by use of phorphoramidite chemistries and the like, or any sequence that hybridizes to the sequence as set forth in SEQ ID NO:1 under stringent conditions. The modified AlfAFP protein, AlfAFP1, exhibits enhanced antifungal activity compared to that of the native AlfAFP, in particular greater than two fold and more particularly greater than about three to about seven fold greater activity.

The nucleic acid sequences contemplated herein also have utility as probes and as primers in nucleic acid hybridization embodiments. As such, it is contemplated that nucleic acid segments that comprise a sequence region that consists of at least a 14 nucleotide long contiguous sequence that has the same sequence as, or is complementary to, a 14 nucleotide long contiguous DNA segment of SEQ ID NO:1 will find particular utility. Longer contiguous identical or complementary sequences, e.g., those of about 20, 30, 40, 50, 100 bp, etc. (including all intermediate lengths and up to and including the full-length sequence of from about nucleotide 1 through about nucleotide 135 as set forth in SEQ ID NO:1) will also be of use in certain embodiments. The ability of such nucleic acid probes to specifically hybridize to antifungal protein-encoding sequences will enable them to be of use in detecting the presence of complementary sequences in a given sample. However, other uses are envisioned, including the use of the sequence information for the preparation of mutagenesis primers, or primers for use in preparing other genetic constructions.

In another embodiment of the present invention, it is contemplated that recombinant vectors may be made that contain the nucleotide sequence disclosed herein to facilitate overexpression studies of the modified AlfAFP gene and for plant transformation. The recombinant vectors may comprise a promoter that helps express the gene in plants, a structural AlfAFP1 nucleotide sequence of the present invention comprising SEQ ID NO:2 and a transcription termination signal. For plant transformation, the vector may also comprise an intron and/or an untranslated leader sequence within the expression cassette from which the AlfAFP1 protein is expressed. An exemplary intron may be a wheat, rice, maize, or *arabidopsis* hsp70 intron.

In a further embodiment, the present invention also provides microorganisms and plants transformed with nucleotide sequences encoding the antifungal polypeptide of the present invention comprising the sequence as set forth in SEQ ID NO:2.

In a yet further embodiment, the present invention comprises immunodetection methods and associated kits. The proteins of the present invention may be used to produce or elicit the production of antibodies that bind specifically and with high affinity to the proteins of the present invention, including monoclonal and polyclonal types of antibodies. Antibodies prepared in accordance with the present invention may be employed to detect alfalfa plant antifungal proteins or alfalfa plant antifungal protein-related epitope-containing peptides. The present invention contemplates methods and kits for screening samples suspected of containing alfalfa plant antifungal protein polypeptides or alfalfa plant antifungal protein-related polypeptides, or cells producing such polypeptides. A kit may contain one or more antibodies of the present invention, and may also contain reagent(s) for detecting an interaction between a sample and an antibody of the present invention. The provided reagent(s) can be radio-, fluorescently- or enzymatically-labeled. The kit can contain a known radiolabeled agent capable of binding or interacting with a nucleic acid or antibody of the present invention.

In a yet still further embodiment, an antifungal composition, comprising an antifungal effective amount of the isolated antifungal polypeptides of the present invention, is contemplated. Preferred compositions comprise the amino acid sequence shown in SEQ ID NO:2 and an acceptable carrier. The antifungal composition may be used for inhibiting the growth of, or killing, pathogenic fungi. The compositions can be formulated by conventional methods such as those described in, for example, Winnacker-Kuchler (1986); van Falkenberg (1972-1973); and K. Martens (1979). Necessary formulation aids, such as carriers, inert materials, surfactants, solvents, and other additives are also well known in the art, and are described, for example, in Winnacker-Kuchler (1986). Using these formulations, it is also possible to prepare mixtures of the present antifungal polypeptides with other anti-fungal-active substances, fertilizers and/or growth regulators, etc., in the form of finished formulations or tank mixes.

Antifungal compositions contemplated herein also include those in the form of host cells, such as bacterial and fungal cells, capable of producing the present antifungal polypeptide, which can colonize roots and/or leaves of plants. Examples of bacterial cells that can be used in this manner may include strains of *Agrobacterium, Arthrobacter, Azospyrillum, Clavibacter, Escherichia, Pseudomonas,* and— *Rhizobacterium*. Examples of fungal cells that can be used in this manner include, e.g., yeast, basidiomycetes, ascomycetes, and the like.

Methods are also contemplated for introducing the nucleotide sequences of the present invention into a plant and for producing a transgenic plant that expresses a nucleic acid segment encoding the alfalfa plant antifungal proteins of the present invention which exhibit improved antifungal activity in comparison to the native alfalfa antifungal protein AlfAFP. The process of producing the transgenic plants is well known in the art.

A method of controlling fungal damage to a plant is also contemplated, comprising providing to the plant a polypeptide comprising or consisting essentially of the amino acid sequence shown in SEQ ID NO:2. In this method, the polypeptide may be provided to the plant locus by plant-colonizing microorganisms that produce the antifungal polypeptide, by applying a composition comprising the isolated polypeptides thereto, or by expressing a nucleotide sequence encoding the polypeptide, a fusion polypeptide, or a chimeric protein comprising the polypeptide as set forth in SEQ ID NO:2 from about amino acid position 1 through about amino acid position 45 within cells of the plant.

Further scope of the applicability of the present invention will become apparent from the detailed description and drawings provided below. However, it should be understood that the detailed description and specific examples, while indicating preferred embodiments of the present invention, are given by way of illustration only since various changes and modifications within the spirit and scope of the invention will become apparent to those skilled in the art from this detailed description.

BRIEF DESCRIPTION OF DRAWING

FIG. 1 shows a cysteine residue alignment of an alfalfa antifungal protein (upper sequence SEQ ID NO:4) with gamma purothionin (γ-thi) (middle sequence SEQ ID NO:5) and radishAFP2 (RsAFP) (lower sequence SEQ ID NO:6).

BRIEF DESCRIPTION OF SEQUENCES

SEQ ID NO:1 represents a native or naturally occurring nucleotide sequence encoding an alfalfa anti-fungal protein, designated herein as AlfAFP.

SEQ ID NO:2 represents the amino acid sequence translation of the open reading frame as set forth in SEQ ID NO:1.

SEQ ID NO:3 represents a nucleotide sequence encoding a D8R amino acid sequence variant of the amino acid sequence as set forth in SEQ ID NO:2, identified herein as AlfAFP1.

SEQ ID NO:4 represents the amino acid sequence translation of the open reading frame as set forth in SEQ ID NO:3.

DETAILED DESCRIPTION

The invention described herein comprises the nucleotide sequence as shown in SEQ ID NO:3 and the amino acid sequence variant encoded by SEQ ID NO:3 as set forth in SEQ ID NO:4. In addition, the invention described herein also includes nucleic acids that encode antifungal proteins which confer resistance to fungal pathogens when incorporated as transgenes and expressed in plants. Agronomic, horticultural, ornamental, and other economically or commercially useful plants, plant parts, and plant products can be made resistant to fungal pathogens by introducing nucleotide sequences encoding such antifungal protein amino acid sequence variants into the plant genome so that the encoded proteins are expressed at a level effective to confer resistance to fungal pathogens.

The inventors herein disclose an improved alfalfa antifungal protein exhibiting antifungal biological activity three to seven fold greater than that of the native protein. In addition, the improved alfalfa antifungal protein exhibits toxicity across a broader host range compared to the antifungal activity exhibited by the native protein, including but not limited to activity against the wheat pathogen *Fusarium culmorum*. The native protein has previously been tested in planta and has been associated with negative agronomic effects in potato. It was believed that expression of an antifungal protein in planta that exhibited a biological activity greater than the native protein would allow for lower expression levels of the improved antifungal protein in planta and thus allow for the reduction or elimination of the negative agronomic effects observed upon expression of the native protein.

Fourteen AlfAFP amino acid sequence variants were constructed, and ten of these variants were tested for antifungal activity in vitro. One of these variants, AlfAFP1, exemplified in SEQ ID NO:4, exhibited a 3-7-fold increase in antifungal activity in vitro. This variant was also active against *Verticillium dahliae* when expressed in potato.

A gene encoding AlfAFP1, including naturally occurring muteins and variants thereof, can be obtained from the chromosomal DNA of a plant species by conventional molecular biological methods and mutated to produce the mutated AlfAFP1 following the method disclosed herein. For example, chromosomal DNA libraries may be constructed in vectors such as the bacteriophage vectors, e.g., lambda.EMBL3 and lambda.gt10, cosmids, or plasmids using methods known in the art (Sambrook et al., 1989). Genes encoding polypeptides having the same as or similar antifungal activity as that of AlfAFP1 can be isolated by PCR performed on chromosomal DNA or chromosomal DNA libraries, or by probe hybridization of genomic DNA libraries. Primers for PCR and probes for hybridization screening can be designed based on the nucleotide sequence of the polypeptide shown in SEQ ID NO:3. The primers should not have self-complementary sequences nor have complementary sequences at their 3' ends in order to prevent primer-dimer formation. The primers may contain restriction sites. The primers are annealed to the DNA and sufficient cycles of PCR are performed to yield a product readily visualized by gel electrophoresis and staining. The primers are generally at least 16 nucleotides in length, typically at least 20 nucleotides in length, preferably at least 24 nucleotides in length, and more preferably at least 28 nucleotides in length. Such primers will be capable of specifically priming genes encoding antifungal polypeptides or proteins having the same or similar antifungal activity as AlfAFP1. The amplified fragments may be purified and inserted into an appropriate vector, and propagated by conventional means known in the art.

For purposes of protection against pathogenic fungi, a preferred gene which may be introduced includes, for example, an alfalfa plant antifungal protein-encoding DNA sequence from plant origin, and particularly one described herein which is obtained from *Medicago* or any of those sequences which have been genetically engineered to decrease or increase the antifungal activity of alfalfa plant antifungal proteins in such a transformed host cell. However, it is believed that highly homologous antifungal proteins with similar antifungal activity will also be found in other plant species, including but not limited to the following: *Arabidopsis*, barley, broccoli, cabbage, canola, carrot, corn, garlic, onion, pea, pepper, potato, rice, soybean, sugarbeet, tobacco, tomato, and wheat; microorganisms such as *Aspergillus, Penicilium, Streptomyces, Alternaria* (—*Alternaria brassicola; Alternaria solani*); *Ascochyta* (*Ascochyta pisi*); *Botrytis* (—*Botrytis cinerea*); *Cercospora* (*Cercospora kikuchii; Cercospora zaea-maydis*);—*Colletotrichum* (*Colletotrichum lindemuthianum*), *Diplodia* (*Diplodia maydis*); *Erysiphe* (*Erysiphe graminis* f. sp. *graminis; Erysiphe graminis* f. sp. *hordei*);—*Fusarium* (*Fusarium nivale; Fusarium oxysporum; Fusarium graminearum; Fusarium culmorum; Fusarium solani; Fusarium moniliforme; Fusarium roseum*);—*Gaeumanomyces* (*Gaeumanomyces graminis* f. sp. *tritici*); *Helminthosporium* (—*Helminthosporium turcicum; Helminthosporium carbonum; Helminthosporium maydis*); *Macrophomina* (*Macrophomina phaseolina; Maganaporthe grisea*);—*Nectria* (*Nectria heamatococca*), *Peronospora* (*Peronospora manshurica; Peronospora tabacina*), *Phoma* (*Phoma betae*); *Phymatotrichum* (*Phymatotrichum omnivorum*), *Phytophthora* (*Phytophthora icinnamomi; Phytophthora cactorum; Phytophthora phaseoli; Phytophthora parasitica; Phytophthora citrophthora, Phytophthora megasperma* f. sp. *sojae; Phytophthora infestans*), *Plasmopara* (—*Plasmopara viticola*); *Podosphaera* (*Podosphaera leucotricha*), *Puccinia* (*Puccinia sorghi; Puccinia striiformis; Puccinia graminis* f. sp. *tritici; Puccinia asparagi; Puccinia recondita; Puccinia arachidis*), *Pythium* (*Pythium aphanidermatum*);—*Pyrenophora* (*Pyrenophora tritici-repentens*); *Pyricularia* (*Pyricularia oryzae*); *Pythium* (*Pythium ultimum*); *Rhizoctonia* (*Rhizoctonia solani; Rhizoctonia cerealis*—); *Scerotium* (*Scerotium rolfsii*); *Sclerotinia* (*Sclerotinia sclerotiorum*); *Septoria* (—*Septoria lycopersici; Septoria glycines; Septoria nodorum; Septoria tritici*); *Thielaviopsis* (*Thielaviopsis basicola*); *Uncinula* (*Uncinula necator*); *Venturia* (—*Venturia inaequalis*); and *Verticillium* (*Verticillium dahliae; Verticillium albo-atrum*); and other nonplant organisms.

In connection with expression embodiments to prepare recombinant proteins and peptides, it is contemplated that longer DNA segments will most often be used, with DNA segments encoding the entire peptide sequence being most preferred. However, it will be appreciated that the use of shorter DNA segments to direct the expression of alfalfa plant antifungal peptides or epitopic core regions, such as may be used to generate anti-alfalfa plant antifungal protein antibodies, also falls within the scope of the invention. DNA segments that encode peptide antigens from about 8 to about 50 amino acids in length, or more preferably, from about 8 to about 30 amino acids in length, or even more preferably, from about 8 to about 20 amino acids in length are contemplated to be particularly useful. Such peptide epitopes may be amino acid sequences that comprise contiguous amino acid sequences from SEQ ID NO:4.

Biologically functional equivalent nucleotide sequences of the present invention include nucleotide sequences encoding conservative amino acid changes within the AlfAFP1 amino acid sequence, producing silent changes therein. Such nucleotide sequences contain corresponding base substitutions compared to nucleotide sequences encoding the AlfAFP1 protein.

In addition to nucleotide sequences encoding conservative amino acid changes within the AlfAFP1 polypeptide sequence, biologically functional equivalent nucleotide sequences of the present invention include nucleotide sequences containing other base substitutions, additions, or deletions. These include nucleic acids containing the same inherent genetic information as that contained in SEQ ID NO:3 and which encode peptides, polypeptides, or proteins conferring fungal resistance the same as or similar to that of the AlfAFP1 protein upon host cells and plants. Such nucleotide sequences can be referred to as "genetically equivalent modified forms" of the sequence shown in SEQ ID NO:3, and can be identified by the methods described herein.

Variations made in the cDNA, plasmid DNA, genomic DNA, synthetic DNA, or other nucleic acid encoding the AlfAFP1 protein preferably preserve the reading frame of the coding sequence. Furthermore, these variations preferably do not create complementary regions that could hybridize to produce secondary mRNA structures, such as loops or hairpins, that would adversely affect mRNA translation. Although sites selected for amino acid variation can be predetermined, it is not necessary that the nature of the variations per se be predetermined. For example, in order to select for optimum characteristics of variations at a given site, random mutagenesis can be conducted at the target codon. Alternatively, nucleotide sequence variations can be introduced at particular loci by synthesizing oligonucleotides containing a variant sequence, flanked by restriction sites enabling ligation to fragments of the variant AlfAFP protein coding sequence of the present invention. Following ligation, the resulting reconstructed nucleotide sequence encodes a derivative form of the AlfAFP1 protein having the desired amino acid insertion, substitution, or deletion. In either case, the expressed variant can be screened for desired antifungal activity by the methods known in the art.

Specific examples of useful genetically equivalent modified forms of SEQ ID NO:3 include DNAs having a nucleotide sequence which exhibits a high level of homology, i.e., sequence identity, to SEQ ID NO:3. Such genetically equivalent modified forms can be readily isolated using conventional DNA-DNA or DNA-RNA hybridization techniques (Sambrook et al., 1989) or by amplification using PCR methods. These forms should possess the ability to confer resistance to fungal pathogens when introduced by conventional transformation techniques into plant cells normally sensitive to such pathogens.

In the present invention, sequence similarity or identity can be determined using the "BestFit" or "Gap" programs of the Sequence Analysis Software Package, Genetics Computer Group, Inc., University of Wisconsin Biotechnology Center, Madison, Wis. 53711.

The fragments and variants of the AlfAFP1 protein may be encoded by cDNA, plasmid DNA, genomic DNA, synthetic DNA, or mRNA. In the present invention, nucleic acids biologically functional equivalent to the DNA of the AlfAFP1 variant protein having the nucleotide sequence shown in SEQ ID NO:4 may include: a) DNAs having a length which has been altered either by natural or artificial mutations such as partial nucleotide deletion, insertion, addition, or the like, so that when the entire length of SEQ ID NO:3 is taken as 100%, the biologically functional equivalent sequence has an approximate length of 60-120% of that of SEQ ID NO:3, preferably 80-110% thereof; or b) nucleotide sequences containing partial (usually 20% or less, preferably 10% or less, more preferably 5% or less of the entire length) natural or artificial mutations so that such sequences code for different amino acids, but wherein the resulting polypeptide retains the antifungal activity of AlfAFP1.

In the present invention, the methods employed to create artificial nucleotide sequence variations are not specifically limited, and such variations can be produced by any of the means conventional in the art. For example, the nucleotide sequence encoding an alfalfa antifungal protein may be treated with appropriate restriction enzymes so as to insert or delete appropriate DNA fragments so that the proper amino acid reading frame is preserved. Subsequent to restriction endonuclease treatment, the digested DNA can be treated to fill in any overhangs, and the DNA religated. Nucleotide sequence variations can also be introduced at particular loci by synthesizing oligonucleotides containing a variant sequence flanked by restriction sites enabling ligation to fragments of the native AlfAFP cDNA or genomic coding sequence. Following ligation, the resulting reconstructed sequence encodes a derivative having the desired amino acid insertion, substitution, or deletion. Alternatively, oligonucleotide-directed site-specific or segment-specific mutagenesis procedures can be employed to produce an altered cDNA or genomic DNA sequence having particular codons altered according to the substitution, deletion, or insertion desired.

Exemplary methods of making the alterations described above are disclosed by Ausubel et al. (1995); Bauer et al. (1985); Craik (1985); Frits Eckstein et al. (1982); Sambrook et al. (1989); Smith et al. (1981); Osuna et al. (1994); and Walder et al. (1986). Biologically functional equivalents to the DNA sequence disclosed herein produced by any of these methods can be selected for by assaying the peptide, polypeptide, or protein encoded thereby.

Biologically functional equivalent forms of the DNA encoding the AlfAFP1 protein include nucleotide sequences that encode peptides, polypeptides, and proteins that react with, i.e., specifically bind to, antibodies raised against either the native AlfAFP protein or against the AlfAFP1 amino acid sequence variant protein, and that exhibit the same or similar antifungal activity as the AlfAFP1 polypeptide. Such antibodies can be polyclonal or monoclonal antibodies.

Due to the degeneracy of the genetic code, i.e., the existence of more than one codon for most of the amino acids naturally occurring in proteins, other DNA (and RNA) sequences that contain essentially the same genetic information as the DNA of the present invention, and which encode substantially the same amino acid sequence as that encoded by the nucleotide sequence of SEQ ID NO:2, can be used in practicing the present invention. This principle applies as well to any of the other nucleotide sequences discussed herein.

Biologically functional equivalent forms of the DNA of the present invention also include synthetic DNAs designed for enhanced expression in particular host cells. Synthetic DNAs designed to enhance expression of the antifungal protein in a particular host should therefore reflect the pattern of codon usage in the host cell.

Other biologically functional equivalent forms of the DNA of SEQ ID NO:3 useful in the present invention include those which have been modified to encode conjugates with other peptides, polypeptides, or proteins, thereby encoding fusion products therewith.

Although one embodiment of a nucleotide sequence encoding the AlfAFP1 variant is shown in SEQ ID NO:3, it should be understood that the present invention also includes nucleotide sequences that hybridize to the sequence of SEQ ID NO:3 and its complementary sequences, and that encode peptides, polypeptides, or proteins having the same or similar antifungal activity as that of the AlfAFP1 variant. Such nucleotide sequences preferably hybridize to SEQ ID NO:3 or its complementary sequences under conditions of moderate to high stringency (see Sambrook et al., 1989). Exemplary conditions include initial hybridization in 6×SSC, 5×Denhardt's solution, 100 mg/ml fish sperm DNA, 0.1% SDS, at 55° C. for sufficient time to permit hybridization (e.g., several hours to overnight), followed by washing two times for 15 min each in 2×SSC, 0.1% SDS, at room temperature, and two times for 15 min each in 0.5-1×SSC, 0.1% SDS, at 55° C., followed by autoradiography. Typically, the nucleic acid molecule is capable of hybridizing when the hybridization mixture is washed at least one time in 0.1×SSC at 55° C., preferably at 60° C., and more preferably at 65° C.

The present invention also encompasses nucleotide sequences that hybridize to the DNA of SEQ ID NO:3 under salt and temperature conditions equivalent to those described above, and that encode a peptide, polypeptide, or protein that has the same or similar antifungal activity as that of the AlfAFP1 protein variant disclosed herein.

The nucleotide sequences described above are considered to possess a biological function substantially equivalent to that of the cDNA of SEQ ID NO:3 encoding the variant AlfAFP1 polypeptide if they encode peptides, polypeptides, or proteins having an antifungal effect differing from that of the variant AlfAFP1 protein by about ±25% or less.

The present invention includes not only the AlfAFP1 coding sequence shown in SEQ ID NO:3 but also biologically functionally equivalent nucleotide sequences. The phrase "biologically functionally equivalent nucleotide sequences" denotes DNAs and RNAs, including genomic DNA, plasmid DNA, cDNA, synthetic DNA, and mRNA nucleotide sequences, that encode peptides, polypeptides, and proteins exhibiting the same or similar antifungal activity as that of the AlfAFP1 protein, i.e., when introduced into host cells in a functionally operable manner so that they are expressed, they produce peptides, polypeptides, or proteins exhibiting antifungal activity at a level sufficient to confer resistance to fungal pathogens upon host cells or plants.

DNA sequence information provided by the invention allows for the preparation of relatively short DNA (or RNA) sequences having the ability to specifically hybridize to gene sequences of the selected polynucleotides disclosed herein. Nucleic acid probes of an appropriate length may be prepared based on a consideration of a selected alfalfa plant antifungal protein gene sequence, e.g., a sequence such as that shown in SEQ ID NO:3. The ability of such DNAs and nucleic acid probes to specifically hybridize to an alfalfa plant antifungal protein gene sequence lends them particular utility in a variety of embodiments. Most importantly, the probes may be used in a variety of assays for detecting the presence of complementary sequences in a given sample.

Nucleic acid molecules having sequence regions consisting of contiguous nucleotide stretches of 10-14, 15-20, 30, 50, or even of 100 nucleotides or so, identical or complementary to DNA sequence of SEQ ID NO:3, are particularly contemplated as hybridization probes for use in, e.g., Southern and Northern blotting. Smaller fragments will generally find use in hybridization embodiments, wherein the length of the contiguous complementary region may be varied, such as between about 10-14 and about 50 or 100 nucleotides, but larger contiguous complementarity stretches may be used, according to the length complementary sequences one wishes to detect.

In certain embodiments, it is advantageous to use oligonucleotide primers. The sequence of such primers is designed using a polynucleotide of the present invention for use in detecting, amplifying or mutating a defined segment of an alfalfa plant antifungal protein gene from *Medicago* using PCR technology. Segments of related alfalfa plant antifungal protein genes from other species may also be amplified by PCR using such primers.

It may also be desirable to incorporate other DNA segments into the genome of a transgenic plant where such DNA encodes other antifungal proteins non-homologous to the disclosed alfalfa antifungal proteins, or various other proteins that improve the quality of plant products or agronomic performance of the plants. Thus other types of proteins encoded by the DNA may include antibacterial, antiviral, antifungal or insecticidal proteins such as *Bacillus thuringiensis* (B.t.) proteins.

Simultaneous co-expression of multiple antifungal and/or other anti-pathogen proteins in plants is advantageous in that it exploits more than one mode of control of plant pathogens. This may, where two or more antifungal proteins are expressed, minimize the possibility of developing resistant fungal species, broaden the scope of resistance and potentially result in a synergistic antifungal effect, thereby enhancing the level of resistance. Co-expression with B.t. insecticidal toxin proteins is expected to provide an additional advantage in providing protection against a wide range of insect larvae. *Bacillus thuringiensis* insecticidal toxin proteins have been expressed in several varieties of plants, including cereal plants.

Other proteins conferring certain advantages may likewise be coexpressed with the DNAs encoding the polypeptides of the present invention; including: (1) DNAs encoding enzymes such as glucose oxidase (which converts glucose to gluconic acid, concomitantly producing hydrogen peroxide which confers broad spectrum resistance to plant pathogens); pyruvate oxidase; oxylate oxidase; cholesterol oxidase; amino acid oxidases; and other oxidases that use molecular oxygen as a primary or secondary substrates to produce peroxides, including hydrogen peroxide; (2) pathogenesis related proteins such as SAR8.2a and SARB.2b proteins; the acidic and basic forms of tobacco PR-1a, PR-1b, PR-1c, PR-1', PR-2, PR-3, PR4, PR-5, PR-N, PR-O, PR-O', PR-P, PR-Q, PR-S, and PR-R proteins; chitinases such as tobacco basic chitinase and cucumber chitinase/lysozyme; peroxidases such as cucumber basic peroxidase; glucanases such as tobacco basic glucanase; osmotin-like proteins; (3) viral capsid proteins and replicases of plant viruses; (4) plant R-genes (resistance genes), such as *Arabidopsis* RPS2 (Bent et al., 1994), *Arabidopsis* RPM 1 (Grant et al., 1995), tobacco N-gene and N'-gene (Whitham et al., 1994), tomato Cf-9 (Jones et al, 1994), flax L6 (Ellis et al, 1995), and rice Xa21 (Song et al., 1995). These genes can be expressed using constitutive promoters, tissue-specific promoters, or promoters inducible by fungal pathogens or other biological or chemical inducers; (5) pathogen Avr genes, such as *Cladosporium fulvum* Avr9 (Van Den Ackerveken et al., 1992), that can be expressed using pathogen- or chemical-inducible promoters; and (6) genes that are involved in the biosynthesis of salicylic acid, such as benzoic acid 2-hydroxylase (Leon et al., 1995). Stabilized RNA"s can be co-expressed along with the protein of the present invention. Such RNA" s could inhibit the growth of or even assist in killing the insect. The present invention contemplates an expression vector comprising a polynucleotide of the present invention. In one embodiment an expression vector is an isolated and purified DNA molecule comprising a promoter operatively linked to an coding region that encodes a polypeptide of the present invention, which coding region is operatively linked to a transcription-terminating region, whereby the promoter drives the transcription of the coding region.

As used herein, the term "operatively linked" means that a promoter is connected to a coding region in such a way that the transcription of that coding region is controlled and regulated by that promoter.

In preferred embodiments, the vector used to express the polypeptide includes a selection marker that is effective in a plant cell, preferably a drug resistance selection marker. One preferred drug resistance marker is the gene whose expression results in kanamycin resistance; i.e., the chimeric gene containing the nopaline synthase promoter, Tn5 neomycin phosphotransferase II (nptII) and nopaline synthase 3' non-translated region (Rogers et al., 1988). Other selectable marker may include hygromycin resistance marker and a herbicide resistance marker.

The 3' end non-translated regions of the chimeric constructs of the present invention should contain a transcriptional terminator, or an element having equivalent function, and a polyadenylation signal that functions in plants to cause the addition of adenylate nucleotides to the 3' end of the mRNA. The variant AlfAFP1 DNA coding sequence may comprise the entire nucleotide sequence shown in SEQ ID NO:3 or any portion thereof that may have functional equivalence, such as truncated versions. Alternatively, it may be desirable to express epitopic regions of the antifungal polypeptide in order to use these peptides to raise antibodies against the antifungal polypeptide of the present invention.

Methods and compositions for transforming a bacterium, a yeast cell, a plant cell, or an entire plant with one or more expression vectors comprising an alfalfa plant antifungal protein-encoding gene segment are further aspects of this disclosure. A transgenic bacterium, yeast cell, plant cell or plant derived from such a transformation process or the progeny and seeds from such a transgenic plant are also further embodiments of the invention.

The formation of transgenic plants may also be accomplished using methods of cell transformation which are known in the art such as *Agrobacterium*-mediated DNA transfer. Alternatively, DNA can be introduced into plants by direct DNA transfer into pollen (Zhou et al., 1983; Hess, 1987; Luo et al., 1988), by injection of the DNA into reproductive organs of a plant (Pena et al., 1987), or by direct injection of DNA into the cells of immature embryos followed by the rehydration of desiccated embryos (Neuhaus et al., 1987; Benbrook et al., 1986).

A transgenic plant of this invention thus has an increased amount of a coding region (e.g., an AlfAFP1 gene) that encodes the variant AlfAFP1 polypeptide of interest. A preferred transgenic plant is an independent segregant and can transmit that gene and its activity to its progeny. The inventors contemplate that the present invention will find particular utility in the creation of transgenic plants of commercial interest including various turf grasses, wheat, corn, rice, barley, oats, potato, soybean, cotton, berries such as strawberries, a variety of ornamental plants and vegetables, as well as a number of nut- and fruit-bearing trees and plants.

The present invention contemplates methods and kits for screening samples suspected of containing alfalfa plant antifungal protein polypeptides or alfalfa plant antifungal protein-related polypeptides, or cells producing such polypeptides. A kit may contain one or more antibodies, at least one of which binds specifically to the AlfAFP1 protein of the present invention, and may also contain reagent(s) for detecting an interaction between a sample and the antibody. The reagent(s) can be radio-, fluorescently- or enzymatically-labeled. The reagent(s) of the kit may be provided as a liquid solution, attached to a solid support or as a dried powder. Preferably, when the reagent(s) are provided in a liquid solution, the liquid solution is an aqueous solution. Preferably, when the reagent(s) provided are attached to a solid support, the solid support can be chromatograph media, a test plate having a plurality of wells, or a microscope slide. When the reagent(s)

provided are a dry powder, the powder can be reconstituted by the addition of a suitable solvent, that may be provided.

An antifungal composition, comprising an antifungal effective amount of one or more of the isolated antifungal polypeptides of the present invention are contemplated. Preferred compositions comprise the amino acid sequence shown in SEQ ID NO:4, and an acceptable carrier. The antifungal composition may be used for inhibiting the growth of, or killing, pathogenic fungi. The compositions can be formulated by conventional methods such as those described in, for example, Winnacker-Kuchler (1986); van Falkenberg (1972-1973); and Martens (1979). Necessary formulation aids, such as carriers, inert materials, surfactants, solvents, and other additives are also well known in the art, and are described, for example, in Winnacker-Kuchler (1986). Using these formulations, it is also possible to prepare mixtures of the present antifungal polypeptide with other antifungally active substances, fertilizers and/or growth regulators, etc., in the form of finished formulations or tank mixes.

Antifungal compositions contemplated herein also include those in the form of host cells, such as bacterial and fungal cells, capable of producing the present antifungal polypeptide, and which can colonize roots and/or leaves of plants. Examples of bacterial cells that can be used in this manner include strains of *Agrobacterium, Arthrobacter, Azospyrillum, Clavibacter, Escherichia, Pseudomonas, Rhizobacterium*, and the like.

Numerous conventional fungal antibiotics and chemical fungicides with which the present antifungal polypeptide can be combined are known in the art and are described in Worthington and Walker (1983). These include, for example, polyoxines, nikkomycines, carboxyamides, aromatic carbohydrates, carboxines, morpholines, inhibitors of sterol biosynthesis, and organophosphorus compounds. Other active ingredients which can be formulated in combination with the present antifungal polypeptide include, for example, insecticides, attractants, sterilizing agents, acaricides, nematocides, and herbicides.

Whether alone or in combination with other active agents, the antifungal polypeptides of the present invention should be applied at a concentration in the range of from about 0.1 mg/ml to about 100 mg/ml, preferably between about 5 mg/ml and about 50 mg/ml, at a pH in the range of from about 3 to about 9. Such compositions may be buffered using, for example, phosphate buffers between about 1 mM and 1M, preferably between about 10 mM and 100 mM, more preferably between about 15 mM and 50 mM.

The variant AlfAFP1 protein of the present invention, and biologically functional equivalents thereof, are therefore expected to be useful in controlling fungi in a wide variety of plants, exemplified by those in the following genera and species:—*Alternaria (Alternaria brassicola; Alternaria solani); Ascochyta (Ascochyta pisi);—Botrytis (Botrytis cinerea); Cercospora (Cercospora kikuchii; Cercospora zaea-maydis); Colletotrichum (Colletotrichum lindemuthianum); Diplodia (Diplodia maydis); Erysiphe (Erysiphe graminis* f. sp. *graminis; Erysiphe graminis* f. sp. *hordei); Fusarium (Fusarium nivale; Fusarium oxysporum; Fusarium graminearum; Fusarium culmorum; Fusarium solani; Fusarium moniliforme; Fusarium roseum); Gaeumanomyces (Gaeumanomyces graminis* f. sp. *tritici);—Helminthosporium (Helminthosporium turcicum; Helminthosporium carbonum; Helminthosporium maydis); Macrophomina (Macrophomina phaseolina; Maganaporthe grisea); Nectria (Nectria heamatococca); Peronospora (Peronospora manshurica; Peronospora tabacina); Phoma (Phoma betae); Phymatotrichum (—Phymatotrichum omnivorum); Phytophthora (Phytophthora cinnamomi; Phytophthora cactorum; Phytophthora phaseoli; Phytophthora parasitica; Phytophthora citrophthora; Phytophthora megasperma* f. sp. *sojae; Phytophthora infestans); Plasmopara (Plasmopara viticola); Podosphaera (Podosphaera leucotricha); Puccinia (Puccinia sorghi; Puccinia striiformis; Puccinia graminis* f. sp. *tritici; Puccinia asparagi; Puccinia recondita; Puccinia arachidis); Pythium (—Pythium aphanidermatum); Pyrenophora (Pyrenophora tritici-repentens);—Pyricularia (Pyricularia oryzae); Pythium (Pythium ultimum); Rhizoctonia (—Rhizoctonia solani; Rhizoctonia cerealis); Scerotium (Scerotium rolfsii); Sclerotinia (Sclerotinia sclerotiorum); Septoria (Septoria lycopersici; Septoria glycines; Septoria nodorum; Septoria tritici); Thielaviopsis (Thielaviopsis basicola); Uncinula (Uncinula necator); Venturia (Venturia inaequalis);* and *Verticillium (Verticillium dahliae; Verticillium albo-atrum).*

Transgenic plants that express antifungal effective amounts of the variant AlfAFP1 protein and biologically functional equivalents thereof can be produced by: (a) transforming plant cells with a recombinant DNA molecule comprising operatively linked in sequence in the 5' to 3' direction: (i) a promoter region that directs the transcription of a gene in plants; (ii) a DNA coding sequence that encodes an RNA sequence which encodes the AlfAFP1 protein or a biologically functionally equivalent thereof having the same or similar antifungal activity as that of the AlfAFP1 protein; and (iii) a 3' non-translated region that encodes a polyadenylation signal which functions in plant cells to cause transcriptional termination and the addition of polyadenylate nucleotides to the 3' end of said RNA sequence; (b) selecting plant cells that have been transformed; (c) regenerating plant cells that have been transformed to produce differentiated plants; and (d) selecting a transformed plant, cells of which express said DNA coding sequence and produce an antifungal effective amount of the AlfAFP1 protein or said biologically functionally equivalent thereof The method of the present invention can be carried out in a variety of ways. The antifungal polypeptides, prepared by any of the methods noted above, may be applied directly to plants in a mixture with carriers or other additives, including other antifungal agents, as is known in the art. Alternatively, the polypeptides may be expressed by bacterial or yeast cells that can be applied to the plant, some of which may be symbiotic with the plants. Plant cells may also be transformed by conventional means to contain DNA encoding the antifungal polypeptides. These may be expressed constitutively, in a tissue-specific manner, or upon exposure of the plant to a fungal pathogen.

The present invention also encompasses the use of any of the DNA sequences or biologically functional equivalents thereof disclosed herein to produce recombinant plasmids, transformed microorganisms, probes, and primers useful in identifying related DNA sequences that confer resistance to fungal pathogens on plant cells, and to produce transgenic plants resistant to such fungal pathogens.

As noted above, the antifungal polypeptides of the present invention may be used in combination with chemicals as well as other antifungal agents, including other peptides, polypeptides, and proteins that exhibit antifungal activity, so as to provide a broader spectrum of activity, i.e., to control additional pathogens, and/or to provide multiple modes of action for the control of the same fungal pathogen. Examples of such other antifungal agents include chitinases, cysteine-rich chitin-binding proteins, β-1,3-glucanases, permuteins (including zeamatins), thionins, ribosome-inactivating proteins, and non-specific lipid transfer proteins.

The following illustrative, non-limiting examples further demonstrate several preferred embodiments of the present invention. Those skilled in the art will recognize numerous equivalents to the specific embodiments described herein. Such equivalents are intended to be within the scope of the present invention and claims.

EXAMPLES

These examples illustrate the identification of an amino acid sequence variant alfalfa antifungal protein exhibiting improved antifungal activity compared to the wild type or native antifungal sequence. The increased biological activity of the variant amino acid sequence provides a means for lower levels of expression of the protein in plants to achieve the same level of antifungal protection to the plant. Lower levels of expression of the protein alleviate negative agronomic effects observed with expression of higher levels of the native protein. The variant amino acid set forth herein exhibits in planta activity against the wheat pathogen *Fusarium culmorum*. In summary, fourteen AlfAFP amino acid sequence variants were constructed and ten of these were tested for antifungal activity in vitro and compared to the activity of the native protein. Surprisingly only one of these variants, AlfAFP1, exhibited a 3-7-fold increase in antifungal activity in vitro. This variant was transformed into and expressed in potato and determined to provide resistance to infection by *Verticillium dahliae*. The amino acid sequence of AlfAFP was aligned to the cysteine residues of the Rs-AFP2 protein used by De Samblanx et al. (1997) and one other plant defensin, γ-thionin (Bruix et. al., 1993). It was expected that substitution of arginine in place of the residues in the AlfAFP corresponding to those result effective residues identified by De Samblanx et al. in the Rs-AFP2 protein would result in improved antifungal activity of the alfalfa antifungal protein AlfAFP. The three sequences were manually aligned in order to conserve the alignment of the eight cysteine residues (FIG. 1). Gaps were manually introduced to maximize sequence conservation first at residues of identity between the cysteines, and second at residues of similarity between the cysteines. Using this sequence alignment, modifications determined by De Samblanx et al. to result in an increase in antifungal activity of Rs-AFP2 were incorporated into the AlfAFP protein. Fourteen (14) amino acid sequence variants of the AlfAFP protein were constructed. The AlfAFP variants were grouped into four classes based on the amino acid sequence modifications incorporated into the variant proteins. The AlfAFP1 variant contained a D8R modification to the amino acid sequence. This modification is unlike the RsAFP2 variant with which De Samblanx et al. demonstrated a 2.5 fold increase in activity in high ionic strength media. The D8R modification changes the net charge of the protein more dramatically than the modification incorporated into the RsAFP2 by De Samblanx et al. and would not be expected to result in an improvement in the antifungal activity of the AlfAFP variant in comparison to the native sequence. Four AlfAFP2 variants were designed to contain the sequence of amino acids that are present in other plant defensins such as RsAFP and γ-thionin but which are conspicuously absent in AlfAFP between amino acid residues F15 and S16 as set forth in SEQ ID NO:2 and in the alignment shown in FIG. 1. Two of the AlfAFP2 modifications incorporate the combinations of serine with arginine or lysine at inserted amino acid positions 16 and 17, shifting the native serine at position 16 to position 18 in these AlfAFP2 variants (AlfAFP2a SerArg inserted between native F15 and S16; AlfAFP2b SerLys inserted between native F15 and S16). The other two AlfAFP2 modifications incorporate the combinations of asparagine with either lysine or arginine at inserted amino acid positions 16 and 17, also shifting the native serine at position 16 to position 18 in the resultant AlfAFP2 variants (AlfAFP2c AsnLys inserted between F15 and S16; AlfAFP2d AsnArg inserted between F15 and S16). De Samblanx et al. demonstrated that positive charges at these positions often result in an increase in antifungal activity under high ionic strength conditions. All AlfAFP2 variants also contain the modification K28L, since DeSamblanx et al. showed that a positively charged residue at the corresponding position in RsAFP2 resulted in a loss of activity under high ionic strength conditions. Additionally, all of the AlfAFP2 variants contain a K25L substitution (with reference to SEQ ID NO:2 and FIG. 1, results in the K25L position having an actual position of L28 with reference to the amino acid sequence of the AlfAFP2 variants) that results in the AlfAFP2 variants exhibiting a net charge that is identical to that of the native AlfAFP protein. Only one AlfAFP3 amino acid sequence variant was designed. A gap in the alignment between RsAFP and AlfAFP after the C33 position in the AlfAFP sequence was partially compensated for by insertion of the amino acids asparagine and tyrosine between C33 and R34 in AlfAFP as set forth in SEQ ID NO:2 and in FIG. 1 (AlfAFP3 AsnTyr inserted between C33 and R34). No other modifications are included in the AlfAFP3 variant. The modifications resulting in the AlfAFP3 variant emulates the RsAFP2 variant amino acid sequence containing an arginine at position 39 that DeSamblanx et al. determined also provided a 2.5 fold increase in antifungal activity under high ionic strength conditions. Eight AlfAFP4 variants were constructed. These variants contain various combinations of the amino acid sequence modifications that are exhibited by the AlfAFP2 variants and the AlfAFP3 variant, along with a variant sequence incorporating phenylalanine in place of the native aspartate proximal to the carboxy-terminal end of the AlfAFP protein sequence (D35 or D36 as set forth in SEQ ID NO:2 and in FIG. 1), referred to herein with reference to the position of the variation within the variant, i.e., a D39F or D40F substitution. The D40F substitution was incorporated because DeSamblanx et al. disclosed that a substitution of phenylalanine for valine at position 40 as set forth in the RsAFP2 amino acid sequence variant resulted in a 10-fold decrease in bioactivity under high ionic strength conditions. All AlfAFP4 variants contain the AsnTyr insertion present in ALfAFP3, as well as the K25L substitution present in the AlfAFP2 variants. In addition, the AlfAFP4a-d variants contain a D36F substitution (with reference to SEQ ID NO:2) and the AlfAFP4e-h variants contain a D35F substitution (with reference to SEQ ID NO:2). The difference between each of these two sets of AlfAFP4 variants resides in the combinations of amino acids inserted as set forth in the ALFAFP2a-d variants, in particular with reference to the amino acids identified as being inserted between F15 and S16 as set forth in SEQ ID NO:2 and in FIG. 1. AlfAFP4a and e contain the AlfAFP2a insertions and substitutions, AlfAFP4b and f contain the AlfAFP2b insertions and substitutions, AlfAFP4c and g contain the AlfAFP2c insertions and substitutions, and AlfAFP4d and h contain the AlfAFP2d insertions and substitutions. All nucleotide sequences described and used herein were derived from the native AlfAFP coding sequence and modified using thermal amplification mutagenesis primers to encode the variant AlfAFP amino acid set forth as described herein. These sequences were introduced into the plasmid vectors pPIC9 and pGAP (INVITROGEN). The resulting recombinant plasmids were constructed in these base vectors and maintained in the *E. coli* strain XL1-Blue according to the manufacturers"

instructions. These vector constructs contained origins of replication that enable replication and expression of the desired genetic elements in *Pichia* yeast systems. *Pichia pastoris* strains KM71 and GS115 (INVITROGEN) were maintained on YPD (1% yeast extract, 2% peptone, 2% dextrose) or MDH (1.34% yeast nitrogen base (YNB), $4\times10^{-5}$% biotin, 1% dextrose, and 0.004% histidine) plates (15 g/L agar) grown at 30 C and stored at 4 C. Recombinant strains were maintained on MD plates (MDH minus histidine). *Pichia pastoris* is not particularly amenable to long-term storage although intermediate storage (6-12 months) was accomplished by ten fold concentration of an overnight culture brought to a final concentration of 25% glycerol. The cultures were slow cooled (–1C/min) 0/N to –80C and then transferred to the vapor phase of a liquid nitrogen assisted freezer (–140C). All constructs expressing either the native AlfAFP (as set forth in SEQ ID NO:2) or amino acid sequence variant forms of the AlfAFP protein were expressed as peptide fusions that were targeted for secretion in the *Pichia* yeast expression system. The AlfAFP coding sequences were linked in frame and downstream of a sequence encoding a yeast alpha mating factor signal peptide that was also linked at it"s 3" end to a sequence encoding an amino acid sequence that represents a KEX2 peptidase cleavage sequence. 10 μg of purified plasmid was linearized with Sal1, precipitated with glycogen, and resuspended in 10 μL of water, before being used for electroporation into *Pichia* yeast according to standard *Pichia* yeast system procedures. A similarly treated hollow vector control was used to assess the transformation efficiency for each transformation reaction. Transformation reactions were plated directly onto MD plates for selection of transformants that arise as individual colony forming units. Ten colonies from each electroporation reaction were selected and inoculated into 25 mL minimal growth media (BMG: 100 mM potassium phosphate pH 6.0, 1.34% YNB, $4\times10^{-5}$% biotin, and 1% glycerol) in 50 mL conical tubes and grown for 48 hours at 30 C, aerated at 250 rpm by orbital shaking. The cultures were harvested by low speed centrifugation. Pellets were resuspended in 5 mL of the appropriate induction media and cultured for another 3-6 days. Buffered minimal methanol media (BMM: 100 mM potassium phosphate pH 6.0, 1.34% YNB, $4\times10^{-5}$% biotin, and 0.5% methanol) was used for pPIC9 derived vectors while buffered minimal glucose (BMG: 100 mM potassium phosphate pH 6.0, 1.34% YNB, $4\times10^{-5}$% biotin, and 0.5% glucose) was used for pGAP9 derived vectors. Each culture was sampled (100 μL) at 24 hour intervals, and methanol induced cultures were supplemented with 25 μL 100% methanol before expression was allowed to continue. Each sample was microcentrifuged at maximum speed for 2 minutes and the conditioned media was assayed by ELISA and/or silver-stained SDS-PAGE for the presence and concentration of AlfAFP specific protein. The antifungal bioassay was performed in 96-well, half-area plates in a total volume of 20 μL. Concentrated spores of *Fusarium graminearum* or *Fusarium culmorum* were prepared from 2-3-week old wheat agar plates, titrated to $7\times10^4$ spores/mL, and frozen for future use. Sporangia of *Verticillium dahliae* were prepared from 2-3-week old potato dextrose agar plates and titrated to a concentration of approximately $7\times10^4$ spores/mL. Each assay consisted of 10 μL of concentrated spore/sporangia stock. Proteins and buffer were used to adjust the final volume to 20 μL. Assays were scored visually on an inverted microscope at 24 and 48 hours and the minimal concentration for fungal growth inhibition was recorded. Approximately 10 fold concentrated conditioned media from transformed yeast cultures were dialyzed against 2000-4000 volumes 20 mM Tris pH 7 using Pierce dialysis cassettes with a 2000 molecular weight cutoff. The dialysis buffer was replaced 3 times before samples were assayed in the bioassay previously described. Similarly treated hollow vector controls were used for comparison. AlfAFP protein samples were purified from small cultures of *Pichia* recombinants that were grown in 250 mL baffled flasks containing 125 mL BMG at 30 C for 24-48 hours with vigorous shaking (250-300 rpm). The cultures were induced in 25 mL of BMM, supplemented with 100% methanol daily to a final concentration of 0.5%, and harvested after 4-6 days. For larger quantities, 1 L cultures were grown in 2 L baffled flasks and induced in 250 mL volumes in half liter flasks. Crude supernatants of *Pichia* expressing AlfAFP or AlfAFP variants were collected by centrifugation of 50 mL cultures 6 days post-induction. The supernatant was saved and prepared for purification by dialysis against 50 mM Tris-HCl at pH 7.0. Fifty mL of the supernatant were dialyzed overnight against 4 L of buffer with 3 buffer changes. After dialysis, the entire supernatant was loaded onto a UnoQ column (BioRad) equilibrated with 50 mM Tris-HCl at a pH to match the crude supernatant of interest. The column was washed with 5 column volumes of 50 mM Tris-HCl, pH 7.0. The column was then eluted in step gradients of increasing NaCl concentration from 0.5 M NaCl to 2.0 M NaCl. Fractions that showed absorbance at 280 nm were collected manually and analyzed by SDS-PAGE on 16% Tricine-SDS gels. Fractions containing AFP (anti fungal protein) were then further purified by reverse-phase HPLC using a 1 mL C18 column support. The fractions of interest were pooled and TFA was added to 0.1% v/v. After applying the sample to the column, the column was washed with 10 volumes of water+0.1% TFA or until the absorbance of the outflow was measured to be zero at 214 nm. The column was then eluted in linear steps with increasing concentrations of acetonitrile+0.1% TFA in the following manner: the acetonitrile concentration was increased linearly from 0% to 10% over 1 minute (1 mL/minute flow rate), followed by 10% to 20% over 10 minutes, 20% to 35% over 15 minutes, 35% to 40% over 5 minutes, and finally, 40% to 100% over 10 minutes. Fractions showing absorbance at 214 nm were collected and separated from the bulk of the column eluate. Fractions were dried overnight under vacuum, resuspended in 50 mM Tris-HCl, pH 7.2, and analyzed by SDS-PAGE and Western blot for the presence of ALfAFP or AlfAFP variants. After quantification using BCA protein assay (BioRad), the purified protein samples were assayed for antifungal activity as described above. The broad-spectrum antifungal activity of AlfAFP has been previously reported (PCT International Publication No. WO 98/26083). The activity of several AlfAFP amino acid sequence variants is shown in Tables 2 and 3. Variants were assayed against the target fungi *Fusarium graminearum* and *Verticillium dahliae* in standard media or standard media equilibrated to high ionic strength (media supplemented with 50 mM $K^+$, 1 mM $Ca^{2+}$). Antifungal activity in high ionic strength media has been attributed to better in vivo activity for these proteins (De Samblanx et al. 1997). The AlfAFP variants show a range of activity against both—*Fusarium* and *Verticillium* Antifungal activity against *Fusarium* was reduced for all but 4 of the variants tested (Tables 1 and 2). Only AlfAFP1 demonstrated activity comparable to the native or wild type protein. Surprisingly, however, the AlfAFP1 variant demonstrated a 3-7 fold improvement in activity against *Fusarium* in the presence of high ionic strength media. Table 1 shows the results of several of the amino acid sequence variant AlfAFP proteins against *Verticillium dahliae*. All variants tested exhibited antifungal activity equivalent to or slightly less than the wild type AlfAFP when assayed in standard media. However, when the media was supplemented with Ca—$^{2+}$, AlfAFP1 again demonstrated a 3-fold increase in antifungal activity. All other variants exhibited activity approximately equivalent to the wild type protein in the high ionic strength media. These data suggested that AlfAFP1 may be useful in planta as an antifungal agent that is superior to that of the native AlfAFP protein.

TABLE 1

Activity of AlfAFP and AlfAFP amino acid sequence variants against *Fusarium graminearum*

| AlfAFP Protein | Standard Media | High Ionic Strength Media |
| --- | --- | --- |
| Alf - wt | 10 | 15-20 |
| Alf1 | 5-10 | 25-5 |
| Alf2a | >20 | >>>20 |
| Alf2b | >20 | 20 |
| Alf2c | >20 | >20 |
| Alf2d | >>>20 | >>>20 |
| Alf3 | 20 | >>>20 |
| Alf4a | >>>20 | >>>20 |
| Alf4b | >>>20 | >>>20 |
| Alf4e | 10 | 20 |
| Alf4f | 10 | 20 |

The activity is given as the minimun concentration of protein required to inhibit fungal growth in units of ppm (parts per million).

TABLE 2

Activity of AlfAFP and AlfAFP variants against *Verticillium dahliae*

| AlfAFP Protein | Standard Media | High Ionic Strength Media |
| --- | --- | --- |
| Alf - wt | 5 | 15 |
| Alf1 | 5 | 5 |
| Alf4e | 10 | 15 |
| Alf4f | 5 | >20 |

The activity is given as the minimum concentration of protein required to inhibit fungal growth in units of ppm (parts per million).

Based on the data presented above, a plant expression vector was constructed for use in transforming potato to express the AlfAFP1 variant in planta. Transgenic potato plants were prepared using *Agrobacterium tumefaciens* mediated plant transformation methods. Potato plants expressing the AlfAFP1 variant protein showed improved control of disease symptoms caused by artificial infection with *Verticillium dahliae* (data not shown). The in planta results are consistent with the in vivo data presented above, suggesting that the AlfAFP1 protein could be used to control fungal disease caused by *Verticillium dahliae* when expressed in plants.

A structural model of the AlfAFP1 variant protein was generated using the NMR structure of RsAFP1 (Fant et al, 1998), a sequence alignment between the two proteins, and the Homology module of the InsightII software (Accelyris, San Diego, Calif.). Two structurally adjacent sites that are responsible for antifungal activity have been proposed in the plant defensin RsAFP2 from radish (De Samblanx et al., 1997). The first of these sites is the loop connecting β-strand 1 with α-helix 1. The AlfAFP1 variant protein that demonstrated an increase in antifungal activity in vitro as well as activity in vivo, contains an amino acid substitution within a proposed similar loop in the AlfAFP1 protein. The AlfAFP1 substitution is similar in position to the G9R substitution DeSamblanx et al. in the RsAFP2 variant, yet is quite different in its nature in that the DeSamblanx et al. substitution results in the modification of a neutral charged residue to an alkaline/basic charged residue while the AlfAFP1 substitution results in a more dramatic modification from an acidic residue to a basic residue. This substitution in the AlfAFP protein would be expected to either dramatically reduce or eliminate the antifungal activity of the protein if the aspartate at position 8 as set forth in SEQ ID NO:2 was relevant in the activity of the protein. In contrast, the result of the D8R substitution in AlfAFP resulting in the sequence as set forth in SEQ ID NO:4 produced a protein that surprisingly exhibited an improvement in antifungal activity. The other AlfAFP variants that are described herein which emulated the DeSamblanx et al. modifications to RsAFP and which resulted in improved RsAFP activity should have resulted in an improvement in AlfAFP antifungal activity. In contrast, most of the modifications to AlfAFP resulted in decreased or abolished antifungal activity.

The second site proposed by DeSamblanx et al. for antifungal activity in RsAFP is located in the loop between β-strand 2 and β-strand 3. In the results of the study described hereinabove, the predicted improvement of antifungal activity as a result of the amino acid sequence modifications in this region in the AlfAFP protein were not observed. These results suggest that the two-site hypothesis may not completely describe the structural requirements for antifungal activity of these cysteine rich peptides referred to as plant defensins.

It will be understood by those skilled in the art that, without departing from the scope and spirit of the present invention and without undue experimentation, the present invention can be performed within a wide range of equivalent parameters. While the present invention has been described in connection with specific embodiments thereof, it will be understood that it is capable of further modifications. The present invention covers any uses, variations, or adaptations of the invention following the principles of the invention in general. Various permutations and combination of the elements provided in all the claims that follow are possible and fall within the scope of this invention.

All publications and patents mentioned in this specification are herein incorporated by reference as if each individual publication or patent was specially and individually stated to be incorporated by reference.

REFERENCES

Ausubel et al., Current Protocols in Molecular Biology, John Wiley and Sons, Inc., 1995.
Bauer et al., Gene, 37:73, 1985.
Becker et al., Plant J., 5:299, 1994.
Bent et al., Science, 265:1856-1860, 1994.
Bol et al., Ann. Rev. Phytophathol, 28:113-138, 1990.
Boorsma et al., J. Histochem. Cytochem., 23:200-207, 1975.
Bower and Birch, Plant J., 2:409, 1992.
Bowles, Ann. Rev. Biochem., 59:873-907, 1990.
Brears et al., Agro-Food-Industry Hi-Tech., 10-13, 1994.
Broekaert et al., Plant Physiol., 108:1353-1358, 1995.
Broekaert et al., Crit. Rev. in Plant Sci. 16: 297-323, 1997-
    [0094] Bruix et al., Biochemistry 32715-724, 1993.
Bytebier et al., Proc. Natl. Acad. Sci. U.S.A., 84:5345, 1987.
Campbell et al., Plant Physiol., 92:1-11, 1990.
Cassas et al., Proc. Natl. Acad. Sci. U.S.A., 90:11212, 1993.
Celano et al., Biotechniques, 15:27-28, 1993.
Chiang et al., Molecular Plant-Microbe Interactions, 4:324-331, 1991.
Christensen et al., Plant Mol. Biol., 18:675, 689, 1992.
Christou et al., Bio/Technology, 9:957, 1991.

Christou, Agro Food Industry Hi Tech, 17, 1994.
Compton T., In: PCR™ Protocols, A Guide to Methods and Applications, Innis et al., Eds., Academic Press, San Diego, 39-45, 1990.
Craik, BioTechniques, 3:12-19, 1985.
Cuypers et al, Mol. Plant-Microbe Interact, 1:157-160, 1988.
De la Pena et al., Nature, 325:274, 1987. De Samblanx et al., J. Biol. Chem. 272, 1171-1179, 1997.
Ditta et al., Proc. Natl. Acad. Sci. U.S.A., 77:7347, 1980.
Ellis et al., Proc. Natl. Acad. Sci. U.S.A., 92: 4185, 1995.
Fant et al., J. Mol. Biol. 279257-270, 1998.
Fisk and Dandekar, Scientia Horticulturae, 55:5-36, 1993.
Fling et al., Nucl. Acids Res., 13:7095-7106, 1985.
Fraley et al., Proc. Natl. Acad. Sci. U.S.A., 80:4803, 1983.
Frits Eckstein et al., Nucleic Acids Research, 10:6487-6497, 1982.
Fritzemeier et al., Plant Physiol., 85: 3441, 1987.
Fromm et al., Bio/Technology, 8:833, 1990.
Gao et al., Nature Biotech. 18: 1307-1310, 2000.
Gasser and Fraley, Science, 244:1293, 1989.
Gordon-Kamm et al., Plant Cell, 2:603, 1990.
Grant et al., Science, 269:843-846, 1995.
Horn et al., Plant Cell Rep., 7: 469, 1988.
Horsfall et al., Phytopathology, 35:655, 1945.
Joaquim et al., Phytopathology, 81:552-558, 1991.
Jones et al., Science, 266:789-793, 1994.
Kawasaki E. S., In: PCR™ Protocols, A Guide to Methods and Applications, Innis et al., Eds., Academic Press, San Diego, 21-27, 1990.
Kay et al., Science, 236:1299, 1987.
Kobayashi et al., Neurochem. Int. 18: 525-534, 1991.
Koncz et al., Mol. Gen. Genet., 204:383-396, 1986.
Koziel et al., Bio/Technology, 11:194, 1993.
Laemmli, Nature, 227:680-685, 1970.
Leon et al., Proc. Natl. Acad. Sci. U.S.A., 92:10413-10417, 1995.
Linthorst, Crit. Rev. Plant Sci., 10:123-150, 1991.
Logemann et al., Plant Cell, 1:151-158, 1989.
Luo and Wu, Plant Mol. Biol. Rep., 6:165, 1988.
Mandel et al., Plant Mol. Biol, 29:995-1004, 1995.
Martens K., Spray Drying Handbook, Third Edition, G. Goodwin, Ltd., London, 1979.
Martini et al., Mol. Gen. Genet., 263:179, 1993.
Matton et al., Mol. Plant-Microbe Interact, 2:325-331, 1989.
McElroy et al., Plant Cell, 2:163-171, 1990.
Murashige et al., Physiol. Plant., 15:473, 1962.
Murray et al., Nucl. Acids. Res., 17: 477-498, 1989.
Osuna et al., Critical Reviews In Microbiology, 20:107-116, 1994.
Pyee et al., Plant J., 7:49-59, 1995.
Rhodes et al., Science, 240:204, 1988.
Samac et al., Plant Cell, 3:1063-1072, 1991.
Sambrook et al., Molecular Cloning: A Laboratory Manual, Second Edition, Cold Spring Harbor Laboratory Press, Cold Spring Harbor, N.Y., 1989.
Schroder et al., Plant J., 2:161-172, 1992.
Scoble et al., In: A Practical Guide to Protein and Peptide Purification for Microsequencing, P. Matsudaira, Ed., Academic Press, Inc., San Diego, 125-153, 1993.
Smith et al, In: Genetic Engineering: Principles and Methods, Setlow et al., Eds., Plenum Press, N.Y., 1-32, 1981.
Somers et al., Bio/Technology, 10:1589, 1992.
Song et al., Science, 270:1804-1806, 1995.
Stalker et al., Mol. Gen. Genet., 181:8-12, 1981.
Stone et al., In: A Practical Guide to Protein and Peptide Purification for Microsequencing, P. Matsudaira, Ed., Academic Press, Inc., San Francisco, 55-56, 1993.
Terras et al., J. Biol. Chem., 267:15301-15309, 1992.
Toriyama et al., Bio/Technology, 6:10, 1988.
Troy Weeks et al., Plant Physiol., 102:1077, 1993.
Van Den Ackerveken et al., Plant J., 2:359, 1992.
Van Falkenberg, Pesticide Formulations, Second Edition, Marcel Dekker, N.Y., 1972-1973.
Vasil et al., Bio/Technology, 10:667, 1992.
Walder et al., Gene, 42:133, 1986.
Wan and Lemaux, Plant Physiol., 104:37, 1994.
Wang et al., Bio/Technology, 10:691, 1992.
Watkins, Handbook of Insecticide Dust Diluents and Carriers, Second Edition, Darland Books, Caldwell, N. J. Weigel, Annu. Rev. Genetics, 29:19-39, 1995.
Whitham et al., Cell, 78:1101-1115, 1994.
Winnacker-Kuchler, Chemical Technology, Fourth Edition, Volume 7, Hanser Verlag, Munich, 1986.
Winter, Mol. Gen. Genet., 221:315-319, 1988.
Worthington and Walker, The Pesticide Manual, Seventh Edition, British Crop Protection Council, 1983.
Zhang and Wu, Theor. Appl. Genet., 76: 835, 1988.
Zhang et al., Plant Cell Rep., 7: 379, 1988.
Zhong et al., Plant Cell Rep., 13:1, 1993.
U.S. Pat. No. 4,940,840.
WO 98/26083.
WO 93/05153.
WO 93/05153.
WO 92/04449.
WO 88/00976.
WO 90/07001.
WO 91/06312.
WO 91/18984.
EPO 0 290 123.
EPO 0 292 435.
EPO 0 307 841.
EPO 0 332 104.
EPO 0 392 225.
EPO 0 418 695.
EPO 0 440 304.
EPO 0 448 511.

What is claimed is:

1. A polypeptide comprising the amino acid sequence as set forth in SEQ ID NO: 4, wherein said polypeptide inhibits the growth of a plant pathogenic fungus.

2. A composition comprising a polypeptide and a solvent, wherein said polypeptide comprises SEQ ID NO: 4, and wherein the composition inhibits the growth of a plant pathogenic fungus.

3. The composition of claim 2 wherein said plant pathogenic fungus comprises *Phytophthora infestans, Fusarium graminearum, Fusarium moniliforme, Verticillium dahliae* or *Stagnospora nodorum*.

* * * * *

SEQUENCE LISTING

```
<160> NUMBER OF SEQ ID NOS: 6

<210> SEQ ID NO 1
<211> LENGTH: 135
<212> TYPE: DNA
<213> ORGANISM: Medicago sativa
<220> FEATURE:
<221> NAME/KEY: CDS
<222> LOCATION: (1)..(135)
```

```
<400> SEQUENCE: 1 aga aca tgt gag aat ttg gca gat aaa tat agg gga cca tgc ttt agt      48
Arg Thr Cys Glu Asn Leu Ala Asp Lys Tyr Arg Gly Pro Cys Phe Ser
1               5                   10                  15 ggt tgt gac act cac tgc aca acc aaa gag aac gca gtt agt gga agg      96
Gly Cys Asp Thr His Cys Thr Thr Lys Glu Asn Ala Val Ser Gly Arg
            20                  25                  30 tgt agg gac gac ttc cgc tgc tgg tgt act aaa aga tgt                 135
Cys Arg Asp Asp Phe Arg Cys Trp Cys Thr Lys Arg Cys
        35                  40                  45

<210> SEQ ID NO 2
<211> LENGTH: 45
<212> TYPE: PRT
<213> ORGANISM: Medicago sativa

<400> SEQUENCE: 2

Arg Thr Cys Glu Asn Leu Ala Asp Lys Tyr Arg Gly Pro Cys Phe Ser
1               5                   10                  15

Gly Cys Asp Thr His Cys Thr Thr Lys Glu Asn Ala Val Ser Gly Arg
            20                  25                  30

Cys Arg Asp Asp Phe Arg Cys Trp Cys Thr Lys Arg Cys
        35                  40                  45

<210> SEQ ID NO 3
<211> LENGTH: 135
<212> TYPE: DNA
<213> ORGANISM: Artificial Sequence
<220> FEATURE:
<223> OTHER INFORMATION: AlfAFP1 D8R
<220> FEATURE:
<221> NAME/KEY: CDS
<222> LOCATION: (1)..(135)
<223> OTHER INFORMATION: AlfAFP1 D8R

<400> SEQUENCE: 3 aga aca tgt gag aat ttg gca aga aaa tat agg gga cca tgc ttt agt      48
Arg Thr Cys Glu Asn Leu Ala Arg Lys Tyr Arg Gly Pro Cys

```
<213> ORGANISM: Hordeum vulgare

<400> SEQUENCE: 5

Lys Ile Cys Arg Arg Ser Ala Gly Phe Lys Gly Pro Cys Met Ser
1               5                   10                  15

Asn Lys Asn Cys Ala Gln Val Cys Gln Gln Glu Gly Trp Gly Gly
            20                  25                  30

Asn Cys Asp Gly Pro Phe Arg Arg Cys Lys Cys Ile Arg Gln Cys
        35                  40                  45

<210> SEQ ID NO 6
<211> LENGTH: 51
<212> TYPE: PRT
<213> ORGANISM: Raphanus sativus

<400> SEQUENCE: 6

Gln Lys Leu Cys Glu Arg Pro Ser Gly Thr Trp Ser Gly Val Cys Gly
1               5                   10                  15

Asn Asn Asn Ala Cys Lys Asn Gln Cys Ile Asn Leu Glu Lys Ala Arg
            20                  25                  30

His Gly Ser Cys Asn Tyr Val Phe Pro Ala His Lys Cys Ile Cys Tyr
        35                  40                  45

Phe Pro Cys
    50
```